(12) United States Patent
Staetz et al.

(10) Patent No.: US 8,153,145 B2
(45) Date of Patent: *Apr. 10, 2012

(54) FORMULATIONS OF BIFENTHRIN AND ENRICHED CYPERMETHRIN

(75) Inventors: Charles A. Staetz, Nevada City, CA (US); Hui S. Yang, Plainsboro, NJ (US); Hylsa Garcia, Elizabeth, NJ (US)

(73) Assignee: FMC Corporation, Philadelphia, PA (US)

( * ) Notice: Subject to any disclaimer, the term of this patent is extended or adjusted under 35 U.S.C. 154(b) by 626 days.

This patent is subject to a terminal disclaimer.

(21) Appl. No.: 12/158,454

(22) PCT Filed: Dec. 21, 2006

(86) PCT No.: PCT/US2006/049061
§ 371 (c)(1),
(2), (4) Date: Nov. 13, 2008

(87) PCT Pub. No.: WO2007/076027
PCT Pub. Date: Jul. 5, 2007

(65) Prior Publication Data
US 2009/0170935 A1    Jul. 2, 2009

Related U.S. Application Data

(60) Provisional application No. 60/752,979, filed on Dec. 22, 2005.

(51) Int. Cl.
*A01N 25/02* (2006.01)
*C07C 253/32* (2006.01)

(52) U.S. Cl. .................................. 424/405; 558/354
(58) Field of Classification Search .................. None
See application file for complete search history.

(56) References Cited

U.S. PATENT DOCUMENTS

| | | | | | |
|---|---|---|---|---|---|
| 2,898,267 | A | * | 8/1959 | Lindner | 514/568 |
| 3,912,494 | A | * | 10/1975 | Fischer | 504/128 |
| 4,997,970 | A | * | 3/1991 | Ager, Jr. | 558/354 |
| 5,028,731 | A | | 7/1991 | Glenn | |
| 5,164,411 | A | | 11/1992 | Baum | |
| 5,443,835 | A | * | 8/1995 | Winston | 424/407 |
| 6,048,542 | A | * | 4/2000 | Eagles et al. | 424/405 |
| 6,114,284 | A | * | 9/2000 | Fujisawa et al. | 504/140 |
| 2001/0008873 | A1 | | 7/2001 | Shafer et al. | |
| 2005/0069567 | A1 | | 3/2005 | Ballard et al. | |
| 2005/0215433 | A1 | * | 9/2005 | Benitez et al. | 504/254 |

FOREIGN PATENT DOCUMENTS
WO     WO 03053345 A2 *  7/2003

OTHER PUBLICATIONS

U.S. Appl. No. 12/158,487, filed Oct. 2008, Herrick et al.*

* cited by examiner

*Primary Examiner* — Sreeni Padmanabhan
*Assistant Examiner* — Svetlana M Ivanova
(74) *Attorney, Agent, or Firm* — FMC Corporation

(57) ABSTRACT

The present invention is directed to novel insecticidal compositions comprising bifenthrin and enriched cypermethrin, the compositions are physically stable when diluted with water.

3 Claims, No Drawings

FORMULATIONS OF BIFENTHRIN AND ENRICHED CYPERMETHRIN

This application claims the benefit of U.S. Provisional Application No. 60/752,979 filed Dec. 22, 2005.

FIELD OF THE INVENTION

The present invention relates to the field of insecticides and insecticidal compositions. In particular, the invention relates to novel insecticidal compositions comprising bifenthrin and enriched cypermethrin that are physically stable when diluted with water.

BACKGROUND OF THE INVENTION

To enable the efficient elimination or controlling of unwanted insects in agricultural and other applications, it is desirable to use effective chemical insecticides on these unwanted pests. Formulations containing multiple insecticides are desirable in order to broaden the spectrum of economically important insect, mite, and other pest species killed or controlled and take advantage of the individual pesticidal characteristics of each of the active ingredients.

Compositions containing two or more insecticides have been practiced in the art, but problems with the physical stability of such mixtures in water have caused application and efficacy issues. When traditional insecticidal compositions are combined, the combined components (surfactants, viscosity modifiers, wetting agents) of both may cause accelerated physical degradation (phase separation) of the mixture when diluted in low to moderately hard water. This physical degradation can occur in the mix tanks prior to application on plants or another locus where control is desired. Often this problem goes unnoticed and a uniform application of the insecticide mixture is not achieved, yielding inadequate efficacy.

Typically, in commercial applications, the insecticidal formulation comprises less than one percent of the tank mixture to keep the cost of the formulation low, while still yielding spectrum and onset of visual symptomology benefits. The physical stability of the formulation when diluted with water is a key problem in the art.

SUMMARY OF THE INVENTION

In accordance with the present invention, novel liquid formulations comprising bifenthrin and enriched cypermethrin have been found which have significantly improved the physical stability when diluted in water.

DETAILED DESCRIPTION OF THE INVENTION

The present invention is directed to novel insecticidal compositions comprising bifenthrin and enriched cypermethrin in an insecticidal formulation having significantly improved physical stability when the composition is diluted in water.

zeta-Cypermethrin is a potent and quick acting insecticide, which controls a broad spectrum of chewing, sucking and flying insects. In addition to controlling chewing, sucking and flying insects, the pyrethroid bifenthrin is also active against a number of key mite pests and exhibits a longer residual activity than zeta-cypermethrin.

The term "bifenthrin" means 2-methylbiphenyl-3-ylmethyl (Z)-(1RS)-cis-3-(2-chloro-3,3,3-trifluoroprop-1-enyl)-2,2-dimethyl cyclopropanecarboxylate.

The term "cypermethrin" means the synthetic pyrethroid (R,S)-α-cyano-3-phenoxybenzyl-(1RS)-cis-trans-3-(2,2-dichlorovinyl)-2,2-dimethylcyclopropanecarboxylate which consists of a mixture of eight isomers, each of which are present in approximately the same amounts. Since the discovery and commercialization of cypermethrin, products containing increased amounts of certain isomers have been developed. As used herein, the term "enriched cypermethrin" refers to the following:

alpha-cypermethrin which is a racemate comprising (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate;

beta-cypermethrin which is a reaction mixture comprising two enantiomeric pairs in a ratio of about 2:3 (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate with (S)-α-cyano-3-phenoxybenzyl (1R)-trans-3-(2,2-dichlorovinyl)-2,2-dimethylcyclopropanecarboxylate and (R)-α-cyano-3-phenoxybenzyl (1S)-trans-3-(2,2-dichlorovinyl)-2,2-dimethylcyclopropanecarboxylate;

theta-cypermethrin which is a 1:1 mixture of the enantiomers (R)-α-cyano-3-phenoxybenzyl (1S)-trans-3-(2,2-dichlorovinyl)-2,2-dimethylcyclopropanecarboxylate and (S)-α-cyano-3-phenoxybenzyl (1R)-trans-3-(2,2-dichlorovinyl)-2,2-dimethylcyclopropanecarboxylate; and zeta-cypermethrin which is (R,S)-α-cyano-3-phenoxybenzyl-(1RS)-cis-trans-3-(2,2-dichlorovinyl)-2,2-dimethylcyclopropanecarboxylate which has been enriched in the 1R-cis-S and 1R-trans-isomers].

A particular form of "zeta-cypermethrin" is (R,S)-α-cyano-3-phenoxybenzyl-(1RS)-cis-trans-3-(2,2-dichlorovinyl)-2,2-dimethylcyclopropanecarboxylate which has been enriched in the 1R-cis-S and 1R-trans-S isomers by the processes disclosed in U.S. Pat. Nos. 5,164,411, 5,028,731 and 4,997,970. A most preferred form of "zeta-cypermethrin" is the cypermethrin isomer mixture prepared by the process disclosed in U.S. Pat. No. 4,997,970 starting with a 55/45 cis/trans mixture of cypermethrin with a catalytic amount of tricaprylylammonium chloride (Aliquat® 336, Aldrich Chemical Co.) and sodium carbonate in n-heptane. This process and the subsequent isolation procedure produces zeta-cypermethrin containing a small amount, usually 0.6% to 1.3%, of the catalyst. The presence of this catalyst adds to the complexity of producing a formulation that is stable when diluted with water.

In a preferred embodiment of the present invention, the bifenthrin and enriched cypermethrin insecticides are present in a combined concentration of from 0.01% by weight to 40% by weight, more particularly, from 0.05% by weight to 30% by weight based upon the total weight of all components in the composition. The ratio of bifenthrin active ingredient (AI) to enriched cypermethrin AI may be from 1/99 to 99/1. Preferably the ratio of bifenthrin AI to enriched cypermethrin AI is from 1/4 to 4/1. More preferably the ratio is from 1/3 to 3/1.

In one aspect, the present invention is directed to an insecticidal composition comprising bifenthrin and enriched cypermethrin, an aromatic or aliphatic solvent, an acid, severely solvent refined light and heavy paraffinic petroleum oil and a surfactant blend comprising an alkylbenzene sulfonate salt, an ethoxylated castor oil, and an ethoxylated fatty acid or a polyethylene glycol fatty acid ester, wherein said bifenthrin and enriched cypermethrin insecticides are present, collectively, in an insecticidally effective amount.

Preferably, the aromatic solvent is selected from alkylated naphthalene aromatic and alkylated naphthalene depleted aromatic fluids, for example Aromatic 200 ND Fluid and Aromatic 200 Fluid (both available from ExxonMobil Chemicals). The aliphatic solvent is selected from de-aromatized hydrocarbon fluids, for example, Exxsol D series fluids (available from ExxonMobile Chemicals), isoparaffinic fluids, for example Isopar fluids (available from ExxonMobile Chemicals), and hydrocarbon fluids with very high normal paraffin content, for example, Norpar fluids (available from ExxonMobile Chemicals). The aromatic or aliphatic solvent is present in a concentration of from 10% to 90% by weight and preferably, 40% to 55% by weight, based on the total weight of all components in the composition. The most preferred solvent is an alkylated naphthalene depleted aromatic fluid present in a concentration of from 44% to 47%

Preferably, the alkylbenzene sulfonate salt is the amine or calcium salt of a branched or linear alkylbenzene sulfonate. More preferred, the alkylbenzene dodecylbenzene sulfonate salt is a branched dodecylbenzene sulfonate aminoethylethanolamine or calcium salt, for example, Agnique ABS 70AE and Agnique ABS 60 BC (available from Cognis Corporation) and Rhodacal 70 (available from Rhodia Corporation). The dodecylbenzene sulfonate, or salt thereof, may be present in a concentration of from 1.5% to 4.5% by weight, based on the total weight of all components in the composition.

The ethoxylated castor oil may be one or more ethoxylated castor oils selected from the group of ethoxylated castor oils having an EO number of 8 to 50. Preferably the ethoxylated castor oil has an EO number of 15 to 40 and most preferred an EO number of 20 to 40, for example, Agnique CSO-25 and Agnique CSO-36 (available from Cognis Corporation). The ethoxylated castor oil may be present in a concentration of from 1.5% to 4.5% by weight, based on the total weight of all the components in the composition.

The ethoxylated fatty acid is preferably a $C_9$ to $C_{20}$ ethoxylated fatty acid, for example, stearic acid monooleate, stearic acid dioleate, and stearic acid monosterate. The polyethylene glycol fatty acid ester is selected from polyethylene glycol monooleates having an average $M_n$ of 100 to 800, preferably an average $M_n$ of 300 to 500, and most preferred, an average $M_n$ of 400, for example, Agnique PEG 400MO (available from Cognis Corporation). The ethoxylated fatty acid or the polyethylene glycol fatty acid ester may be present in a concentration of from 0.10% to 0.60% by weight, based on the total weight of all the components in the composition.

The severely solvent refined light and heavy paraffinic petroleum oil is a mixture of from 80% to 100% by volume light paraffinic petroleum oil and from 0% to 20% by volume of heavy paraffinic petroleum oil, for example, Sunpray 6N (available from Sunoco, Inc.), Orchex 796 (available from ExxonMobile USA) and BVA Spray 10 (available from BVA Oils). The severely solvent refined light and heavy paraffinic petroleum oil mixture may be present in a concentration of from 20% to 30% by weight of all the components in the total formulation, preferably in a concentration of from 24% to 26% by weight, based on the total weight of all the components in the composition.

An acid is used to buffer the formulation in order to stabilize the zeta-cypermethrin from epimerizing to less active isomers. The acid is preferably acetic acid or glacial acetic acid and is present in a concentration of from 0.01% to 0.15% by weight, based on the total weight of all the components in the composition.

The insecticidal formulation may further comprise additional components such as an anti-freeze agent, an anti-foam agent and/or a biocide.

A preferred embodiment of this aspect of the invention is an insecticidal emulsifiable concentrate formulation wherein said bifenthrin and enriched cypermethrin insecticides are present in a ratio of 1/4 to 4/1 and a concentration of from 0.05% to 30%, the aromatic solvent is present in a concentration of from 40% to 55%, the acetic acid is present in a concentration of from 0.01% to 0.15%, the severely solvent refined light and heavy paraffinic petroleum oil is present in a concentration of from 20% to 30%, the branched dodecylbenzene sulfonate salt is present in a concentration of from 1.5% to 4.5%, the ethoxylated castor oil or mixture of castor oils is present in a concentration of from 1.% to 4.5% and the polyethylene glycol fatty acid ester is present in a concentration of from 0.10% to 0.60% wherein all %'s are % by weight based upon the total weight of the formulation.

Another aspect of the present invention is directed to an insecticidal composition comprising an aqueous mixture of bifenthrin and enriched cypermethrin, an aromatic solvent, one or more nonionic polymeric surfactants, an antifoam agent, a preservative and glycerine, wherein the bifenthrin and enriched cypermethrin insecticides are present, at least collectively, in an insecticidally effective amount.

The aromatic solvent is selected from alkylated naphthalene aromatic and alkylated naphthalene depleted aromatic fluids, for example Aromatic 200 ND Fluid and Aromatic 200 Fluid (both available from ExxonMobil Chemicals). The aromatic solvent is present in a concentration of from 5% to 30% by weight, preferably 12% to 15% by weight, based on the total weight of all components in the composition.

Preferably, the nonionic polymeric surfactant is one or more surfactants selected from the group consisting of an alkyd polyethylene glycol, for example, Atlox 4914 (available from Uniqema Corporation) and a polyalkylene glycol ether, for example, Atlas G-5000 (available from Uniqema Corporation). Preferably the nonionic polymeric surfactant is present in a concentration of from 3% to 20% by weight preferably from 8% to 12% by weight, based on the total weight of all components in the composition.

The antifoam agent is preferably a silicone containing antifoam agent, for example, Rhodorsil emulsion 1824 antifoam (available from Rhodia Corporation) and Dow Corning AF Emulsion (available from Dow Corning Corporation). Preferably the antifoam agent is present in a concentration of from 0.001% to 1.5% by weight, based on the total weight of all the components in the composition.

The biocide is an isothiazolone mixture, for example, Kathon CG/ICP preservative or Legend MK preservative (available from Rohm and Haas Corporation). Preferably the biocide is present in a concentration of from 0.001% to 1.5% by weight, based on the total weight of all the components in the composition.

The glycerine is preferably refined glycerine, for example, Agnique GLY 99-U glycerine (available from Cognis Corporation). Glycerine is present in a concentration of from 3% to 15% by weight, preferably from 5% to 10% by weight, based on the total weight of all the components in the composition.

Water is used as a diluent and preferably is purified water, for example, deionized or distilled water, and is present in an amount that would dilute the active ingredients to a desired concentration. Preferably water is present in a concentration of from 40% to 60% by weight, based on the total weight of all the components in the composition.

A preferred embodiment of this aspect of the invention is an insecticidal concentrated aqueous emulsion formulation wherein said bifenthrin and enriched cypermethrin insecticides are present in a ratio of from 1/4 to 4/1 and in a concentration of from 0.05% to 30%, the aromatic solvent is present in a concentration of from 12% to 15%, nonionic polymeric surfactant is present in a concentration of from 8% to 12%, the antifoam agent is present in an amount of from 0.001% to 1.5%, the preservative is present in a concentration of from 0.001% to 1.5%, glycerine is present in a concentration of from 5% to 10% and water is present in a concentration of from 40% to 60%, wherein all %'s are % by weight based upon the total weight of all the components in the formulation.

The term "ambient temperature" as utilized herein shall generally mean any suitable temperature found in a laboratory or other working quarter, and is generally not below about 15° C. nor above about 30° C.

The formulations of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

This example illustrates one protocol for the preparation of a 2/1 ratio of bifenthrin to zeta-cypermethrin emulsifiable concentrate formulation of the present invention.

To 42.32 grams of Aromatic 200 ND was added 8.34 grams of melted bifenthrin (95.9% active ingredient) and 11.11 grams of zeta-cypermethrin (36% active ingredient, prepared by the process disclosed in U.S. Pat. No. 4,997,970). The mixture was stirred at ambient temperature with a mechanical stirrer until a homogenous solution formed, at which time 2.52 grams of a branched dodecylbenzene sulfonate salt (Agnique ABS 70AE), 0.28 gram of polyethylene glycol monooleate (Agnique PEG 400MO) 0.84 gram of ethoxylated castor oil (Agnique CSO-36), 1.96 grams ethoxylated castor oil (Agnique CSO-25), 20.00 grams of severely solvent refined light and heavy paraffinic petroleum oil (Sunspray 6N available) and 0.08 gram of acetic acid were added. Upon completion of the addition, the agitation was continued for 10 minutes to obtain a yellowish homogeneous solution.

The following Table 1 sets forth additional formulation examples prepared in the manner of Example 1.

TABLE 1

Bifenthrin and Zeta-Cypermethrin Formulations Containing, By Weight Of All The Components In The Total Formulation: 52.9% Aromatic 200, 25.0% Sunspray 6N and 0.09% Acetic Acid

| Formulation Code | AI* (g) | Agnique ABS70AE (g) | Agnique PEG400MO (g) | Agnique CSO-36 (g) | Agnique CSO-25 (g) |
|---|---|---|---|---|---|
| F2  | 0.31/0.42  | 0.0945 | 0.0105 | 0.0315 | 0.0735 |
| F3  | 0.31/0.42  | 0.021  | 0.042  | 0.084  | 0.063  |
| F4  | 0.31/0.42  | 0.063  | 0.042  | 0.084  | 0.021  |
| F5  | 0.31/0.42  | 0.021  | 0.0315 | 0.084  | 0.0735 |
| F6  | 0.31/0.42  | 0.042  | 0.0105 | 0.084  | 0.0735 |
| F7  | 0.31/0.42  | 0.1155 | 0.042  | 0.0315 | 0.021  |
| F8  | 0.31/0.42  | 0.021  | 0.042  | 0.0735 | 0.0735 |
| F9  | 0.31/0.42  | 0.063  | 0.042  | 0.0315 | 0.0735 |
| F10 | 0.31/0.42  | 0.147  | 0.0105 | 0.0315 | 0.021  |
| F11 | 0.31/0.42  | 0.0945 | 0.0105 | 0.084  | 0.021  |
| F12 | 1.82/16.42 | 1.68   | 0.56   | 1.867  | 1.493  |
| F13 | 16.42/1.82 | 3.92   | 0.112  | 0.871  | 0.697  |
| F14 | 9.12/9.12  | 1.68   | 0.112  | 2.116  | 1.692  |
| F15 | 9.12/9.12  | 1.68   | 0.56   | 1.867  | 1.493  |
| F16 | 16.42/1.82 | 1.68   | 0.112  | 2.116  | 1.692  |
| F17 | 1.82/16.42 | 1.68   | 0.112  | 2.116  | 1.692  |
| F18 | 9.12/9.12  | 3.92   | 0.112  | 0.871  | 0.697  |
| F19 | 1.82/16.42 | 3.92   | 0.112  | 0.871  | 0.697  |
| F20 | 9.12/9.12  | 3.92   | 0.56   | 0.622  | 0.498  |
| F21 | 16.42/1.82 | 1.68   | 0.56   | 1.867  | 1.493  |
| F22 | 16.42/1.82 | 3.92   | 0.56   | 0.622  | 0.498  |
| F23 | 1.82/16.42 | 3.92   | 0.56   | 0.622  | 0.498  |

*Bifenthrin grams (95.5% AI)/zeta-cypermethrin grams (36% AI, prepared by the process disclosed in U.S. Pat. No. 4,997,970)

EXAMPLE 2

Dilution stability studies were conducted using 2.5 mL of the formulation of Example 1 added to 47.5 mL of water with 342 ppm hardness in a 50 mL Nessler tube. The Nessler tube was sealed with a rubber stopper and the contents mixed by inverting the tube ten times. The Nessler tube was placed in a tube rack at ambient temperature and the percent separation was recorded at 2.0 hours and 4.0 hours. The percent separation was calculated by first measuring the height of the separation, if any, then the total height of the mixture. Dividing the separation height by the total height and multiplying by 100 provides the percent separation. Table 2 sets forth the dilution stability percent separation of the formulations described in Example 1 and Table 1. The formulations are identified by the formulation code corresponding to those in Example 1 and in Table 1.

As a control experiment, 6.0 grams of a commercially available formulation of bifenthrin (Capture 2EC® available from FMC Corporation) and 1.2 grams of a commercially available formulation of zeta-cypermethrin (Mustang Max 0.8EC® available from FMC Corporation) were blended together in 1.2 grams of Aromatic 200. The concentration of AI's was similar to the concentration of AI's in formulation code F2. A dilution stability test was performed using 2.5 mL of the control blend in 47.5 mL of water containing 342 ppm hardness as described above. The dilution stability percent separation results of the control experiment are presented in Table 2.

TABLE 2

Percent Separation of Formulation in Water Containing 342 ppm Hardness

| Formulation Code | % Separation | |
|---|---|---|
| | 2.0 Hr | 4.0 Hr |
| F1 | 0 | 0 |
| F2 | 0 | 0 |
| F3 | 3 | 5 |
| F4 | 3 | 6 |
| F5 | 3 | 6 |
| F6 | 3 | 7 |
| F7 | 3 | 6 |
| F8 | 4 | 6 |
| F9 | 2 | 4 |
| F10 | 6 | 10 |
| F11 | 0 | 0 |
| F12 | 0.5 | 4 |
| F13 | 6 | 12 |
| F14 | 0 | 10 |
| F15 | 0 | 6 |
| F16 | 0 | 8 |
| F17 | 0.5 | 4 |
| F18 | 10 | 16 |
| F19 | 10 | 14 |
| F20 | 10 | 18 |
| F21 | 0 | 4 |
| F22 | 14 | 16 |
| F23 | 10 | 16 |
| Control | 47 | 71 |

The novel formulations of the present invention are superior in maintaining the physical stability of a mixture of bifenthrin and zeta-cypermethrin in dilution stability tests when compared to the control dilution stability test.

EXAMPLE 3

This example illustrates one protocol for the preparation of a 3/1 ratio of bifenthrin to zeta-cypermethrin emulsifiable concentrate formulation of the present invention To 45.64 grams of Aromatic 200 was added 11.84 grams of melted bifenthrin (95.9% active ingredient) and 10.42 grams of zeta-cypermethrin (36% active ingredient, prepared by the process disclosed in U.S. Pat. No. 4,997,970). The mixture was stirred at ambient temperature with a mechanical stirrer until a homogenous solution formed at which time 3.48 grams of a branched dodecylbenzene sulfonate salt (Agnique ABS 70AE), 0.35 gram of polyethylene glycol monooleate (Agnique PEG 400M) 1.05 grams of ethoxylated castor oil (Agnique CSO-36), 2.12 grams ethoxylated castor oil (Agnique CSO-25), 25.00 grams of severely solvent refined light and heavy paraffinic petroleum oil (Sunspray 6N) and 0.1 gram of glacial acetic acid was added. Upon completion of the addition, the agitation was continued until a yellowish homogeneous solution was obtained.

EXAMPLE 4

A dilution stability study was conducted using 2.5 mL of the formulation prepared in Example 3 added to 47.5 mL of water with 342 ppm hardness in a 50 mL Nessler tube. The Nessler tube was sealed with a rubber stopper and the contents mixed by inverting the tube ten times. A total of three Nessler tubes were prepared in this manner. One Nessler tube was placed in a tube rack maintained at 0° C., one in a tube rack maintained at ambient temperature and one in a tube rack maintained at 30° C., all were maintained for 24 hours. The percent separation after 24 hours was 0% for each temperature.

EXAMPLE 5

This example illustrates one protocol for the preparation of a 3/1 ratio of bifenthrin to zeta-cypermethrin concentrated aqueous emulsion formulation of the present invention To a vessel equipped with a mechanical stirrer and a homogenizer was added 0.10 gram of a silicone containing antifoam agent (Rhodorsil emulsion 1824 antifoam), 6.0 grams of a polyalkylene glycol ether nonionic polymeric surfactant (Atlas G5000) and 49.15 grams of deionized water. The mixture was stirred and heated at 50° C. to 55° C. While maintaining this temperature, the homogenizer was turned on and a warm (50° C. to 55° C.) mixture of 13.63 grams of alkylated naphthalene depleted aromatic solvent (Aromatic 200 ND), 8.42 grams of zeta-cypermethrin (36% active ingredient, prepared by the process disclosed in U.S. Pat. No. 4,997,970), 10.10 grams of bifenthrin (95.9% active ingredient) and 4.00 grams of alkyd polyethylene glycol nonionic surfactant (Atlox 4914) was added slowly. The mixture was homogenized until a particle size of less than three microns at 90% tile was obtained. The homogenizer was turned off and the stirred mixture was allowed to cool to less than 40° C. at which time 8.5 grams of refined glycerine (Agnique GLY99-U) and 0.10 grams of preservative (Legend MK) were added. The resulting mixture was stirred until a homogenous solution was obtained while cooling to ambient temperature.

EXAMPLE 6

A dilution stability study was conducted using 2.5 mL of the formulation prepared in Example 5 added to 47.5 mL of water with 342 ppm hardness in a 50 mL Nessler tube. The Nessler tube was sealed with a rubber stopper and the contents mixed by inverting the tube ten times. A total of three Nessler tubes were prepared in this manner. One Nessler tube was placed in a tube rack maintained at 0° C., one in a tube rack maintained at ambient temperature and one in a tube rack maintained at 30° C., all were maintained for 24 hours. The percent separation after 24 hours was 0% for each temperature.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:
1. An insecticidal composition comprising:
 a) bifenthrin and zeta-cypermethrin present in a ratio of from 1/4 to 4/1 and in a total concentration of from 0.05% to 30%;
 b) an aromatic solvent present in a concentration of from 40% to 55%;
 c) acetic acid present in a concentration of from 0.01% to 0.15%;
 d) severely solvent refined light and heavy paraffinic petroleum oil in a concentration of from 20% to 30%;
 e) a surfactant blend consisting of:
  a. alkylbenzene sulfonate salt in a concentration of from 1.5% to 4.5%;
  b. ethoxylated castor oil in a concentration of from 1.5% to 4.5%; and c. polyethylene glycol fatty acid ester present in a concentration of from 0.10% to 0.60%;
wherein all % are % by weight based on the total weight.

2. A method for controlling insects comprising applying the composition of claim 1 to a locus where insects are present or are expected to be present.

3. A composition of claim 1 further comprising at least one additional component selected from an anti-freeze agent, an antifoam agent and a biocide.

* * * * *